United States Patent
Cross et al.

(10) Patent No.: US 7,678,546 B1
(45) Date of Patent: Mar. 16, 2010

(54) SOLID-STATE NMR METHOD FOR SCREENING CELL MEMBRANE PROTEIN BINDING DRUG CANDIDATES

(75) Inventors: Timothy Cross, Tallahassee, FL (US);
William W. Brey, Tallahassee, FL (US);
Alexej Smirnov, Raleigh, NC (US);
Eduard Y Chekmenev, Pasadena, CA (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 11/865,302

(22) Filed: Oct. 1, 2007

Related U.S. Application Data (60) Provisional application No. 60/827,552, filed on Sep. 29, 2006.

(51) Int. Cl.
*G01N 33/53* (2006.01)

(52) U.S. Cl. .................. 435/7.1; 435/283.1; 436/501; 436/518; 422/50; 257/9

(58) Field of Classification Search .................. None
See application file for complete search history.

(56) References Cited

OTHER PUBLICATIONS

Chekmenev et al. (The Journal of Magnetic Resonance, vol. 173, 2005, pp. 322-327).*

Hirayama et al. (Analytical Biochemistry, vol. 353, 2006, pp. 99-107).*

Xiao et al. (Journal of Chromatography A, vol. 1067, 2005, pp. 135-143).* et al. (Journal of American Chemical Society, 2004, vol. 12, pp. 9504-9505).*

Watts, Biochemical Society Transactions, 1994, vol. 22, No. 3, pp. 801-805, Abstract Only.*

* cited by examiner

*Primary Examiner*—Lisa V Cook
(74) *Attorney, Agent, or Firm*—Allen, Dyer, Doppelt, Milbrath & Gilchrist, P.A.

(57) ABSTRACT

Disclosed is a method for detection of ligand-cell membrane protein binding by solid state NMR spectroscopy. The method starts by forming a lipid bilayer inside nanopores of an anodic aluminum oxide (AAO) substrate, the lipid bilayer containing a membrane protein sample. The AAO substrate is treated with multiple candidate ligands having potential binding affinity for the membrane protein. Solid-state NMR analysis is performed on the treated AAO/lipid preparation so as to generate an NMR spectrum for the treated membrane protein. The solid-state NMR spectrum of the treated membrane protein is compared with the spectrum of the same preparation of membrane protein in the absence of the ligands. It is then determined whether the solid-state NMR spectrum of the treated membrane protein has shifted from the NMR spectrum of the untreated membrane protein, a shift being indicative of protein binding by the candidate ligand.

2 Claims, 9 Drawing Sheets

SOLID-STATE NMR METHOD FOR SCREENING CELL MEMBRANE PROTEIN BINDING DRUG CANDIDATES

RELATED APPLICATION

This application claims priority from provisional application Ser. No. 60/827,552, which was filed on Sep. 29, 2006, and which is incorporated herein by reference in its entirety.

FIELD OF THE INVENTION

The present invention relates to the field of drug testing, and, more particularly, to a method for detecting a binding interaction between a drug and a cell membrane protein target.

BACKGROUND OF THE INVENTION

Structure-function studies of proteins impose two major requirements on biophysical spectroscopic methods. First, to succeed in such studies, a spectroscopic method should be capable of providing atomic-scale structural data with minimal perturbation to the system. Second, the protein should be maintained in a functionally relevant conformational state. Ideally, one would like to observe detailed molecular structure while the protein progresses through conformational states associated with normal function.

Although modern high-resolution NMR spectroscopy offers unique opportunities for structure-function studies of many water-soluble proteins, membrane proteins are generally less amendable to solution NMR methods. Molecular tumbling of proteins in lipid bilayer systems is insufficient to average out anisotropic magnetic interactions, thus causing broad NMR lines that lead to inevitable loss of resolution and sensitivity. One way to approach the line width problem is to solubilize membrane proteins in mixed detergent micelles that form a shell around the hydrophobic portion of the protein. These detergent-protein complexes may tumble rapidly enough in solution to produce narrow, motionally averaged NMR resonances.

Unfortunately, surrounding some proteins with detergent molecules is known to destabilize functional conformational states and/or perturb the membrane protein tertiary structure (1). There is also growing evidence that many membrane proteins adopt functionally active conformational states only when embedded in or interacting with lipid bilayers of specific composition representative of the native environment (2).

Alternatively, membrane proteins can be studied by solid-state NMR with spectral resolution improved through macroscopic alignment of the surrounding lipid bilayers with respect to the magnetic field axis. Such alignment results in all proteins in the sample having the same polar angle with respect to the bilayer normal perpendicular to the field, therefore decreasing anisotropic line shape contributions. However, longitudinal orientation of the protein in this spherical coordinate system defined by the bilayer normal remains undetermined, and the anisotropy resulting from observations over the longitudinal angle can still lead to line broadening. This remaining anisotropy can be averaged by rapid rotational diffusion of the protein about the lipid bilayer normal (3). Thus, the latter condition constitutes another essential requirement for achieving the best spectral resolution for macroscopically aligned membrane proteins in which nuclear chemical shift tensors are not uniformly aligned with B0.

Generally, lipid bilayer samples are aligned either mechanically by assembling bilayers on planar solid surfaces such as glass (4) or magnetically by forces that arise in external magnetic field for discoidal bilayered micelles (also called bicelles) with sufficient degree of anisotropic magnetic susceptibility (5, 6).

Bicelles can be prepared by mixing long-chain phospholipids such as DMPC (1,2-dimyristoyl-sn-glycero-3-phosphocholine) with a short-chain DHPC (1,2-dihexanoyl-sng-lycero-3-phosphocholine) in a molar ratio greater than approximately 2.5. In these bicelles, DMPC molecules form near planar bilayers that are capped by short-chain DHPC lipids. The negative sign of the bicelles' magnetic susceptibility tensor forces them to align with the bilayer surface parallel to the direction of the magnetic field. Addition of a few mol percent (with respect to the lipids) of certain lanthanide ions flips the bicelle orientation by 90° (7). For solid-state NMR experiments with membrane proteins, the bicelle magnetic field alignment method offers several important advantages including ease of sample preparation, full hydration of lipid bilayers, and long (>1 year) shelf life of biologically stable samples (8). Although several other lipid compositions for bicelles have been reported in the literature, including mixtures that maintain alignment at both acidic and basic pH values (9) and extended temperature range (10), the choice of lipid composition for anisotropic bicelles that would undergo magnetic field alignment remains limited in comparison with the mechanical (or substrate) alignment method. The latter can be successfully employed for bilayers composed from various types of lipids and under an extended range of external conditions such as temperature, ionic strength, pH, etc. (4, 11-13). Therefore, the mechanical alignment method is generally more applicable and is practiced more often in studies of membrane proteins (14, 15).

One significant drawback of the substrate-alignment method derives from the somewhat limited ability to modify the sample hydration, pH, ionic strength, and concentration of molecules in the aqueous phase. Consequently, it is virtually impossible to expose the same sample, without lengthy sample regeneration and realignment, to a variety of water-soluble agents that could be used to trigger changes in membrane protein conformation or function. These limitations of the planar substrate-aligned lipid bilayer samples prevent many applications of high-resolution solid-state NMR methods for detailed structure-function studies of membrane proteins.

Figure 1:
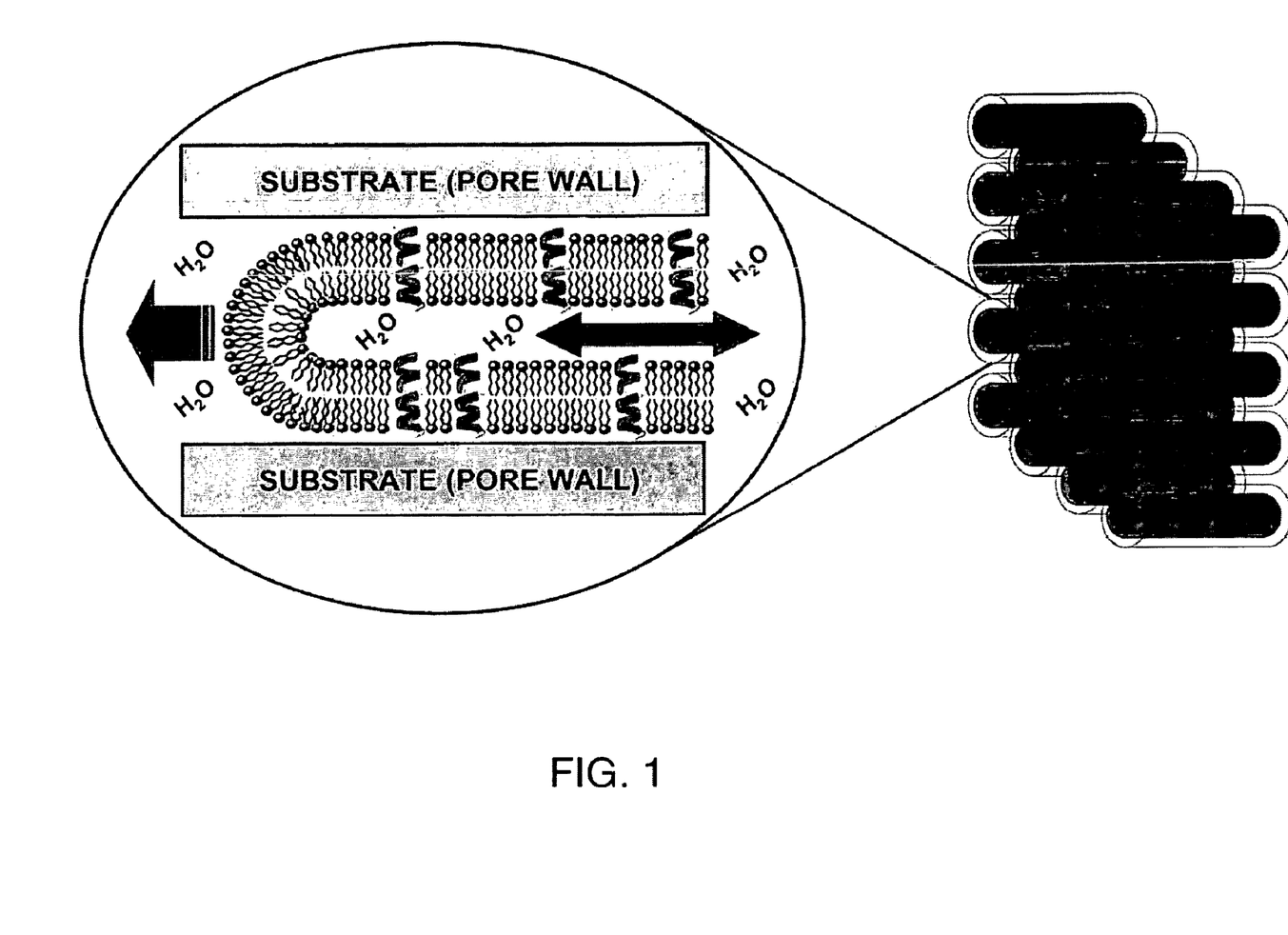
FIG. 1 depicts an embodiment of the present invention wherein a single lipid bilayer aligned inside a nanopore as a multilamellar aqueous dispersion of phospholipids is drawn inside the pores by capillary action and an arrayed structure of nanoporous channels of anodic aluminum oxide membranes is illustrated on the right.

Nanopore-supported lipid nanotube arrays introduced recently (16) provide an attractive way for aligning membrane protein samples for solid-state NMR experiments (17, 18). In brief, it was shown that these macroscopically aligned nano-tubular bilayers are formed by lipid self-assembly inside nano-porous anodic aluminum oxide (AAO) substrates. FIG. 1 shows a cartoon of a single lipid bilayer that is spreading along a nanopore. AAO substrates have aligned through-film nanoporous channels with exceptionally high density. Examination of typical commercial AAO membranes from Whatman International (Maidstone, UK) with scanning electron microscopy (SEM) have shown that the pore density is at least 109 pores/cm2 with an average pore diameter of 177±20 nm (Alaouie, unpublished results). Thus, for 60 μm thick substrate, the total surface area of the nanoporous channels is 334±38 $cm^2$ for each 1×1×0.006 $cm^3$ AAO strip. Elemental chemical analysis has shown that on average up to four lipid nanotubular bilayers can be deposited into each of these AAO nanopores (19). Then such a deposition would provide approximately the same lipid bilayer surface area as depositing 1300 lipid bilayers on top of a 1 $cm^2$ glass slide. Consequently, by stacking a few tens of AAO strips, one can achieve similar lipid volumes in NMR experiments as in the conventional glass plate method. This was indeed confirmed directly by NMR experiments that demonstrated similar signal/noise ratio for AAO-supported and glass-aligned transmembrane domain of the M2 protein of influenza A virus (17).

Recent studies have shown that the new AAO-supported bilayers retain many biophysical properties of unsupported lipid vesicles (19, 20), and they are suitable for aligning membrane proteins for high-resolution multidimensional solid-state NMR studies (17). Detailed NMR (17, 18, 21, 22) and DSC (19, 20) studies provided further characterization of the biophysical properties of such nanotubular bilayers. Specifically, $^{31}$P NMR studies of POPC (1-palmitoyl-2-oleoyl-snglycero-3 phosphocholine) bilayers absorbed into AAO nanopores indicated that some portions of the bilayer surface were inaccessible to $Pr^{3+}$ shift reagent when the bilayer was maintained above the main phase transition temperature. Thus, it was concluded that under the latter conditions the ends of the bilayer tubules must be well sealed against the pore such that the ions cannot penetrate into the water underneath the bilayers (21).

Here, we have reexamined the nanotubular bilayer surface accessibility using $Mn^{2+}$ ions as paramagnetic broadening agents. We demonstrate that, under typical conditions of sample preparation (using DMPC lipids instead of POPC lipids) and handling above and below the main phase transition temperature, both leaflets of nanotubular bilayers are fully accessible to this divalent ion without compromising the macroscopic lipid alignment. Moreover, we demonstrate that the broadening of the $^{31}$P resonances is reversible by a gentle treatment of the AAO stack with the chelating agent EDTA (ethylenediaminetetraacetic acid) followed by a straightforward buffer exchange at temperatures above the main phase transition. This indicates that lipid nano-tube arrays can be prepared with the bilayer surfaces fully accessible to water-soluble molecules. Thus, the high hydration levels of these structures as well as pH and desirable ion and/or drug concentrations can be easily maintained and modified. We are particularly interested in exploring these unique features that permit solvent flow through lipid nano-tube arrays for structure-function studies of membrane proteins by solid-state NMR spectroscopy. Here, we present a demonstration of such experiments at high magnetic field (19.6 T) using $^{17}$O NMR anisotropic chemical shift effects of ion binding to the gramicidin A channel.

The molecular mechanism of ion selectivity in $K^+$ channels is based on the polypeptide backbone carbonyls (23, 24) that provide solvation for $K^+$ on binding. The same fundamental ion-binding interactions are known to contribute to the ion conductance mechanism of other ion transporters including the dimeric gramicidin A (gA) pore, which functions as a monovalent cation-selective channel (25). Gramicidin A is a 15-residue polypeptide with an alternating sequence of D- and L-amino acids: HCO-L-Val$^1$-Gly$^2$-L-Ala$^3$-D-Leu$^4$-L-Ala$^5$-D-Val$^6$-L-Val$^7$-D-Val$^8$-L-Trp$^9$-D-Leu$^{10}$-L-Trp$^{11}$-D-Leu$^{12}$-L-Trp$^{13}$-D-Leu$^{14}$-L-Trp$^{15}$-NHCH$_2$CH$_2$OH (25). In bilayers formed from lipids with fatty acyl chain lengths matching the hydrophobic dimension of the right-handed b-helix, this polypeptide forms a dimer with a 4.5-Å pore accommodating ions and a single file of water molecules (26, 27). Recent NMR studies carried out with gA uniformly aligned in DMPC bilayers using the glass plate method concluded that the carbonyl oxygen of D-Leu$^{10}$ is one of the three carbonyls involved in the ion-binding site at each end of the channel (28, 29).

Specifically, significant perturbation of $^{17}$O anisotropic chemical shift was observed when the gA binding sites were predominantly occupied with two potassium cations (29, 30). Moreover, it was determined that binding of other ions also affects the $^{17}$O NMR chemical shift and that this parameter is a significantly more sensitive indicator for binding events than the $^{15}$N chemical shift typically employed in such studies (29) (E. Y. Chekmenev, L. N. Miller, P. L. Gor'kov, Z. Gan, and T. A. Cross, unpublished results). qq Here we exploit the sensitivity of the $^{17}$O chemical shift to the local ion environment for characterizing cation solvation by the Leu10 carbonyl oxygen that helps to form the binding site for ions in the gA pore. In order to macroscopically align the gA-containing bilayers for NMR experiments and to maintain the gA pore fully hydrated and accessible to various ions, we employed lipid nanotube arrays formed inside nanoporous substrates. With the surfaces of both lipid bilayer leaflets fully accessible to aqueous solutes, we were able to utilize physically the same gA sample in a lipid bilayer environment to study reversible effects of mono- and divalent ion binding on the chemical shift properties of gA Leu$^{10}$ carbonyl oxygen. We also compare the $^{17}$O shifts induced by ion binding to those induced by the binding of protons in the pH range from approximately 1 to 12 and find a significant difference. This unexpected result points to a difference in mechanisms for metal ion (28) and proton (31) conduction by the gA pore. Additionally, temperature and pH ranges for the nanopore alignment method are being established. The effect of lipid bilayer phase on gA Leu$^{10}$ carbonyl $^{17}$O line width also has been investigated.

SUMMARY OF THE INVENTION

With the foregoing in mind, the present invention advantageously provides a method for detection of ligand-cell membrane protein binding by solid state NMR spectroscopy. The method starts by forming lipid bilayers inside nanopores of an anodic aluminum oxide (AAO) substrate, the lipid bilayers containing a membrane protein sample. The AAO/lipid preparation is treated with a candidate ligand having potential binding affinity for the membrane protein. Solid-state NMR analysis is performed on this treated AAO/lipid preparation so as to generate an NMR spectrum for the treated membrane protein. The solid-state NMR spectrum of the treated membrane protein is compared with the spectrum of an identical membrane protein in an untreated preparation. It is then determined whether the solid-state NMR spectrum of the treated membrane protein has shifted from the NMR spectrum of the untreated membrane protein, a shift being indicative of protein binding by the candidate ligand.

In another embodiment of the present invention, a method of screening drug candidates for binding affinity to a cell membrane protein includes supporting lipid bilayers containing the membrane protein in nanopores of a plurality of AAO/lipid preparations. This is followed by treating a portion of AAO/lipid preparations with a drug candidate or a cocktail of drug candidates. The method continues by generating a solid-state NMR spectrum of the membrane protein in the AAO/lipid preparations and generating a solid-state NMR spectrum of the membrane protein in the presence of the candidate drug or drug cocktail. Then, the method ends by comparing the solid-state NMR spectra of the membrane protein from the treated and untreated AAO/lipid preparations and equating a shift in the solid-state NMR spectrum of the treated membrane protein when compared to the untreated membrane protein as an indication of binding of the membrane protein by one of the drug candidates.

In yet another embodiment, the invention includes a solid-state NMR method for screening candidate drug binding affinity for cell membrane proteins. The method begins by introducing self-assembling lipid bilayers into nanopores of anodic aluminum oxide (AAO) support substrates, the lipid bilayer containing a cell membrane protein. The method continues by positioning the preparation in a specially designed NMR flow cell and placing the cell within the radio-frequency solenoid of the NMR instrument. A cocktail of candidate drugs is flowed through the flow cell and the AAO/lipid preparation while in the NMR instrument. A solution free of drugs is then flowed through the cell to wash the candidate drugs out of the preparation so that the cell membrane protein contained therein becomes an untreated control. A solid-state NMR spectrum is then generated for the cell membrane protein in the absence of the potential drugs. Finally, detection of a candidate drug binding to the cell membrane protein is indicated by a shift in the solid-state NMR spectrum of the cell membrane protein from the treated preparations over the untreated control preparations. The process can be repeated without removing the preparation from the NMR instrument.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Materials and Methods

Preparation of $^{17}$O-[D-Leu$^{10}$]-Gramicidin A and Nanopore-Supported Lipid Bilayers.

The $^{17}$O-[D-Leu$^{10}$]-gA was prepared as described previously (29), resulting in material with 57% enrichment of $^{17}$O isotope ($H^{17}_2$O from Cambridge Isotope Labs, Andover, Mass.). The dry peptide was codissolved with DMPC in a 1:16 molar ratio in benzene/ethanol (20:1 v/v) solvent (28) and pipetted onto the nanoporous support. The organic solution containing gA and DMPC was rapidly adsorbed. This commercial substrate, "20 nm" Anodisc 13 membranes (Whatman International), is shaped as disks 13 mm in diameter that are approximately 60 mm thick. For $^{31}$P NMR experiments AAO disks were cut into strips less than 5 mm in width to fit into a rectangular approximately 600 μL sample coil. We have also designed a special coil for $^{17}$O NMR that required no disk cutting. Typically, stacks of up to 40 AAO strips or disks were employed for NMR measurements. The disks have a well-aligned through-film porous structure with nanochannels directed perpendicular to the disk outer surface.

The manufacturer specifies that these nanoporous substrates have a 20-nm filtration diameter cutoff. Examination of these substrates with SEM (A. M. Alaouie, unpublished results) yielded an average pore diameter of 177±20 nm on one side, whereas the average diameter for the filtration side was 29±7 nm. Because the filtration layer is only about 2 mm thick, it is expected that only a negligible amount of lipid will be confined there. After soaking the AAO strips with gA-DMPC solution, we removed the solvent by evaporation in a hood followed by overnight vacuum drying. Substrates with deposited lipids were soaked in water and/or aqueous solutions at 45° C. for at least 4 h. Then 30-40 individual nanoporous AAO strips were stacked, and the sample holder was sealed to maintain a high level of hydration. The sample preparation protocol was also tested with pure DMPC (i.e., gA was not added).

$^{31}$P Solid-State NMR Spectroscopy $^{31}$P Proton-decoupled NMR experiments were performed at 40° C. with a Bruker data acquisition system at 7 T equipped with an NHMFL variable-temperature $^{1}$H/$^{31}$P double resonance static probe (Solid State NMR Facilities at NHMFL. All $^{31}$P chemical shifts are presented relative to the resonance of an 85% solution of H$^{31}$PO$_4$ at 0 ppm.

$^{17}$O Solid-State NMR Spectroscopy $^{17}$O NMR experiments were performed with a Bruker data acquisition system at 19.6 T equipped with an NHMFL variable temperature single resonance static probe tuned to the $^{17}$O operating frequency of 112.5 MHz and utilizing a large, 600-μL, rectangular sample coil (15×9×5 mm) specifically designed to fit the stacks of the Anodisc 13 substrate. The experiments employed a quadrupolar echo (29) with an 8-ms recycle delay without proton decoupling. All $^{17}$O chemical shifts were referenced to liquid H$_2$O at 0 ppm. The temperature was equilibrated for at least 15 min in all experiments. Solute exchange and pH titration experiments were carried out by exposing the Anodisc stacks for a period of at least 1 h to a manifold excess of exchangeable solute molecules at 43° C., that is, well above the main phase transition temperature of DMPC bilayers, T$_m$≈24° C. All $^{17}$O measurements presented here utilized aligned samples oriented in such a way that the magnetic field was parallel to the bilayer surface.

Inherently low NMR sensitivity associated with low-g nuclei such as $^{15}$N, $^{17}$O, and $^{13}$C in proteins dictates the best possible filling factor without compromising sample alignment for NMR experiments. Thus, the signal/noise ratio (S/N) of the $^{17}$O resonance at 19.6 T from the AAO sample preparation protocol described here was compared to that on a conventional glass support (29, 30) and found to be similar, suggesting that approximately the same amount of peptide-containing lipid bilayers was deposited by both methods.

Results

Solvent Accessibility of Nanotubular Lipid Bilayers

Figure 2:
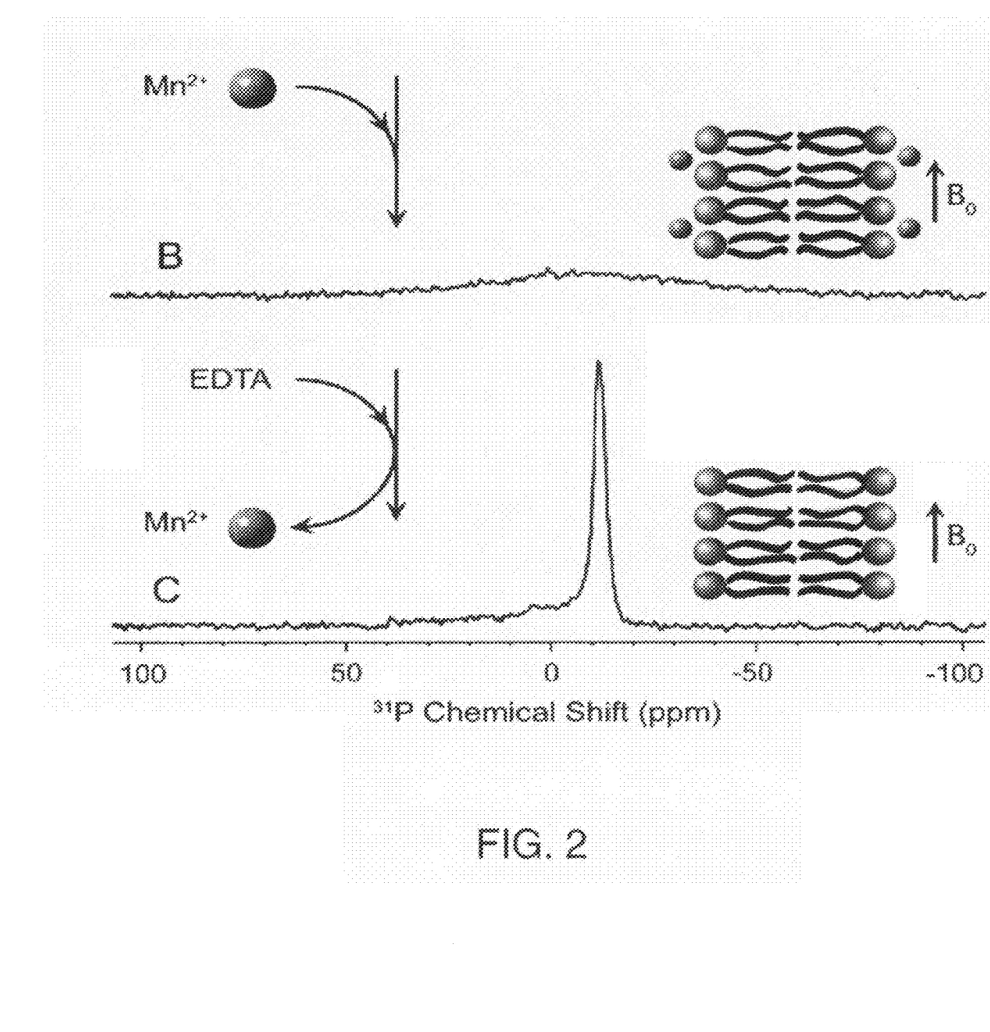
FIG. 2 shows $^{31}$P proton-decoupled 7 T NMR spectra of DMPC bilayers uniformly aligned by the nanoporous support at 25° C. DMPC bilayers were prepared in 10 mM Hepes buffer at pH 5.7 (A) and were exposed to 20 mM $MnCl_2$ for 20 min (B), followed by washing with excess 50 mM dipotassium EDTA salt for 30 min (C); the $^{31}$P chemical shift of 85% $H_3PO_4$ was referenced as 0 ppm.

In order to test whether both leaflets of DMPC bilayers deposited into AAO nanopores are accessible to solvent, we have monitored the $^{31}$P resonances of lipid head groups in the absence and presence of paramagnetic Mn$_{21}$ ions. AAO-supported lipid nanotubes were prepared by deposition from multilamellar DMPC dispersion in a Hepes buffer (16, 17). This method produced fully hydrated and well-aligned nanotubular bilayers as confirmed by $^{31}$P NMR. Specifically, we observed a sharp resonance centered at $\delta_\perp$ 26 −12 ppm when the substrate is aligned with the nanopores parallel to the magnetic field B$_0$ (FIG. 2 A). This is consistent with the bilayers forming cylindrical tubes in the nanopores with the bilayer normal perpendicular to the axis of the nanopore and B$_0$. The broad and much less intense background signal is attributed to phosphate in the AAO matrix that was prepared by an oxalic acid process.

External and inner (sealed) surfaces of lipid bilayers can be discriminated by observing differential broadening and/or shift of lipid resonances in the presence of paramagnetic ions that are likely to interact with the lipid phosphate groups situated at the bilayer surface (32). We have chosen to use paramagnetic Mn$^{2+}$ instead of commonly used lanthanide shift reagents because we were concerned with the possible chelation of the latter trivalent ions by the lipids and/or AAO surfaces. Mn$^{2+}$ ion is known to effectively increase the $^{31}$P T$_2$ relaxation time that leads to excessive line broadening. Indeed, after the lipid nanotube sample was exposed at T≈43° C. to an excess of 20 mM MnCl$_2$ by dipping AAO chips into the solution for 20 min, the narrow lipid $^{31}$P signal was completely broadened (FIG. 2 B). Thus, we can conclude that the lipid head groups of both leaflets of AAO-supported bilayers were fully exposed to the ion-rich buffer and that the sample contained no sealed/inaccessible bilayers even with an average of four nested bilayers.

More importantly, for AAO-supported lipid bilayers prepared and manipulated as described here, such an exposure to metal ions can be reversed without destroying the macroscopic lipid alignment. Specifically, by dipping the AAO chips containing DMPC bilayers with bound Me into a 50 mM solution of dipotassium EDTA salt for 30 min and then immediately immersing the sample in a buffer without paramagnetic ions (all at T≈43° C.), we were able to recover; 70 6 5% of the $^{31}$P signal (FIG. 2 C). This demonstrates effective removal of Mn$^{2+}$ ions from bilayer surfaces. The incomplete recovery is likely caused by a partial washoff of the inner DMPC lipid nanotubes from the AAO nanopores. This was further confirmed in titration experiments with diamagnetic ions: after 15 wash cycles the $^{31}$P signal decreased to approximately 30±5% of the initial intensity.

Reversible Ion Binding to Gramicidin a Pores

Figure 3:
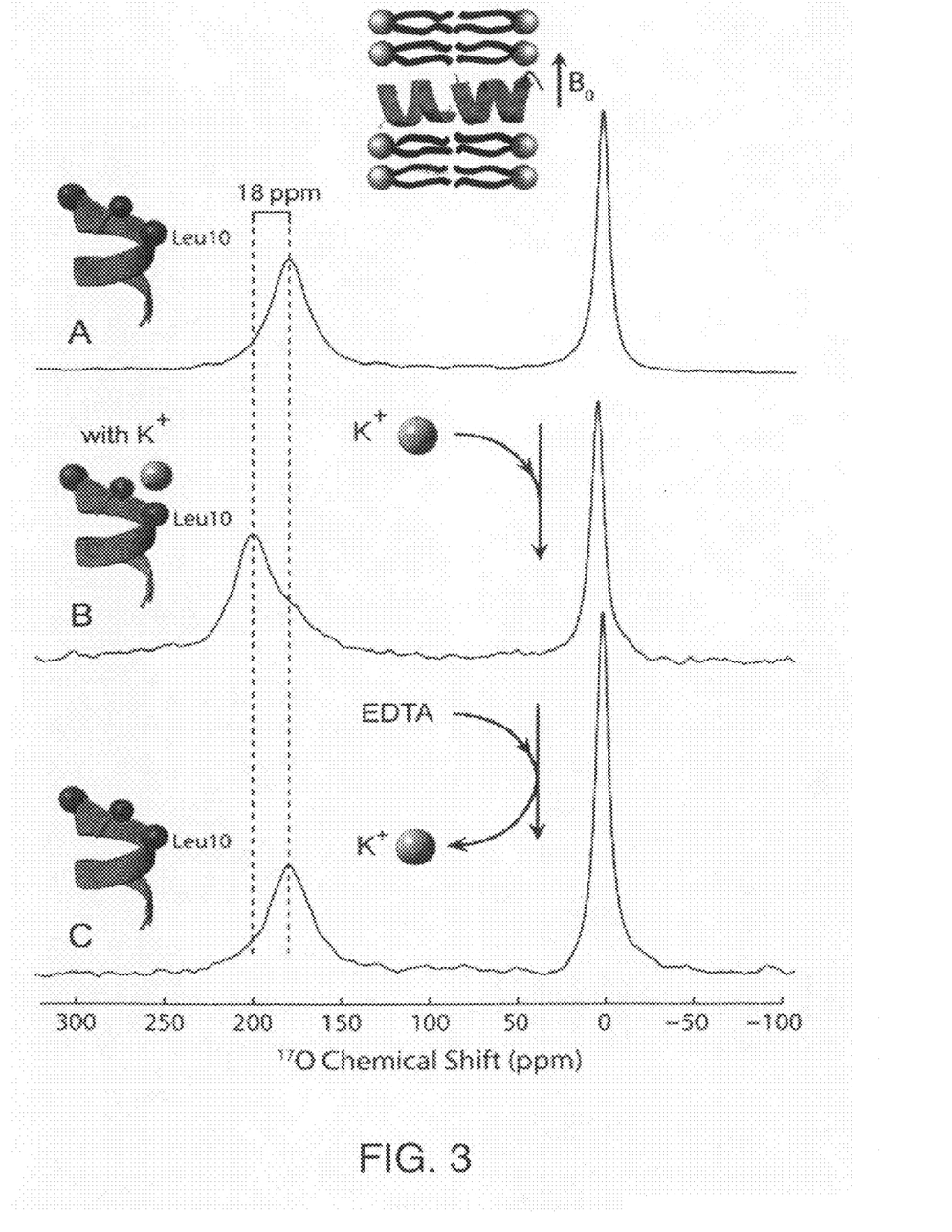
FIG. 3 shows $^{17}$O NMR spectra of $^{17}$O-[D-Leu10]-gA uniformly aligned in DMPC bilayers in the absence and presence of KCl (2.4 M) with a peptide:lipid ratio of 1:16 and excess hydration in AAO-aligned nanotubular bilayers. Spectra were acquired in; 4 h at 40° C. using an NHMFL static probe at 19.6 T and processed with 5 ppm of line broadening; the lipid bilayer sample contained approximately 2 μmol of $^{17}$O-[D-Leu$^{10}$]-gA and was aligned with the magnetic field parallel to the bilayer surface; note that the 0 ppm peak is caused by the natural abundance $^{17}$O water signal and that the δ=196 ppm resonance is somewhat asymmetric and therefore may contain some residual contribution from the δ=178 ppm component corresponding to an unoccupied gA channel.

The Leu$^{10}$ carbonyl in the gramicidin A pore is one of three carbonyl sites involved in K$^+$ binding. We have monitored K$^+$ binding using the $^{17}$O resonance of selectively labeled Lee carbonyls of gramicidin A dimers incorporated into DMPC bilayers and aligned using the AAO method. AAO substrates were positioned with the nanopore channels aligned with B$_0$, and therefore both the bilayer normal and the gramicidin A pore would be approximately perpendicular to B$_0$ (FIG. 3, cartoon at top). If the tumbling of gA around the channel axis is fast, as is the case when DMPC bilayers are in a fluid phase, the gA-Leu$^{10}$ $^{17}$O NMR spectrum should be largely dictated by the average of the two principal axis components of the chemical shift tensor, δ22 and δ33. The latter values were estimated from a powder pattern spectrum observed for a lyophilized gA powder, δ22≈400 and δ33≈−35 ppm (29). For fully hydrated and rapidly tumbling gA in AAO-supported DMPC bilayers oriented in a magnetic field, as shown by a cartoon in FIG. 3, the $^{17}$O resonance is expected to appear at approximately δ=(δ$_{22}$+δ$_{33}$)/2≈183 ppm. The experimentally observed resonance at d 178 ppm (FIG. 3 A) is close to the predicted value. Quadrupole relaxation largely determines the 15-25 ppm width of the $^{17}$O resonance at 19.6 T.

Because the surfaces of nanotubular bilayers are fully accessible to water-soluble molecules, we were able to study the reversible binding effects of K$^+$ to the gramicidin A channel from the $^{17}$O chemical shift using the same sample without losing its macroscopic alignment. When the gADMPC-loaded AAO stack was exposed to 2.4 M KCl to generate approximately double occupancy of K$^+$ in the dimeric channel, or one ion per monomer, a downfield shift of $\Delta\delta \approx 18$ ppm is observed (FIG. 3B). Following K$^+$ removal by the EDTA wash procedure we established for Mn$^{2+}$ ions, the $^{17}$O resonance returns to its original position (FIG. 3 C).

$^{17}$O NMR Gramicidin A Variable Temperature Experiments

Figure 4:
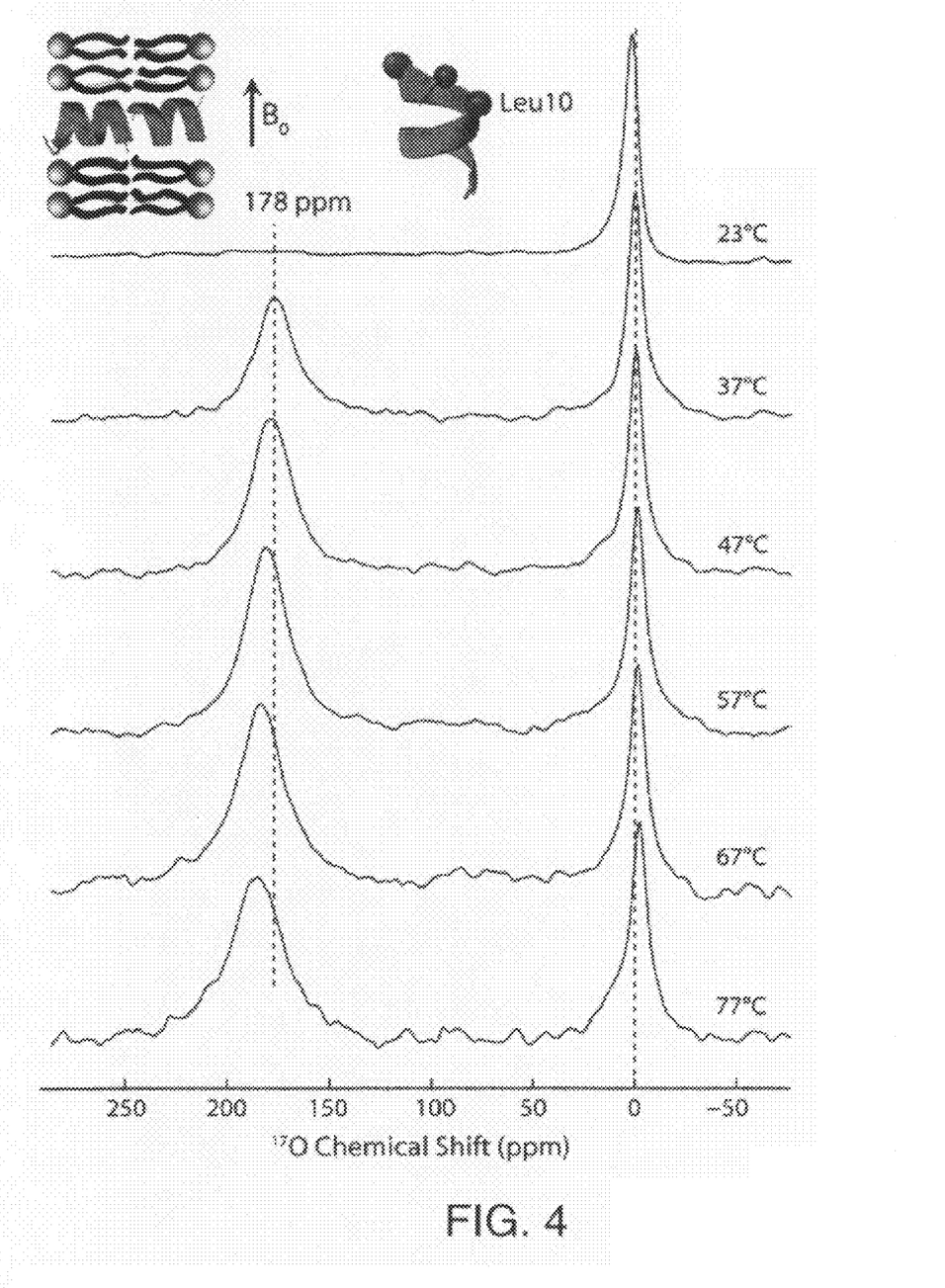
FIG. 4. shows $^{17}$O NMR spectra of $^{17}$O-[D-Leu$^{10}$]-gA uniformly aligned in fully hydrated DMPC bilayers with a peptide:lipid molar ratio of 1:16 at various temperatures; each spectrum was obtained with the NHMFL static probe at 19.6 T using approximately 2 h acquisition and processed with 5 ppm line broadening; the lipid bilayer sample contained approximately 2 μmol of $^{17}$O-[D-Leu$^{10}$]-gA and was aligned with the magnetic field parallel to the bilayer surface. All spectra from 37° C. to 77° C. were normalized by the amplitude of the carbonyl peak.

In order to study the influence of temperature on the $^{17}$O-[DLeu$^{10}$]-gA resonance and stability of the AAO alignment, we have conducted a variable temperature experiment from 23 to 77° C. (FIG. 4). At 23° C. the DMPC bilayer is in the gel phase, and rotational diffusion of the gramicidin A channel around its helical axis is expected to be too slow to effectively average anisotropic $\delta 22$ and $\delta 33$ components. These conditions yield a very broad line that was undetectable at the current noise level (FIG. 4, top). Above the phase transition temperature (T$_m \approx 24°$ C.), a single resonance corresponding to fast motional conditions was detected. Importantly, the single resonance line was observed at temperatures as high as 77° C. (FIG. 4, bottom), indicating exceptional stability and macroscopic alignment of lipid nanotubular structures over a wide temperature range. A deterioration of signal/noise with increase in temperature is also noticeable. This can be attributed to the decrease in population difference between the spin states in equilibrium as well as to the decreased probe performance and higher thermal noise originating from the probe itself. The downfield resonance shift of up to 8 ppm at higher temperatures could be attributed to a variety of factors such as 1), changes in the chemical shift tensor components and 2), contributions of nonaxial tumbling modes. Nonaxial tumbling modes could also be responsible for broadening of the carbonyl 6.178 ppm resonance with temperature.

pH Titration of Gramicidin A Leu$^{10}$ Ion-Binding Site

Figure 5:
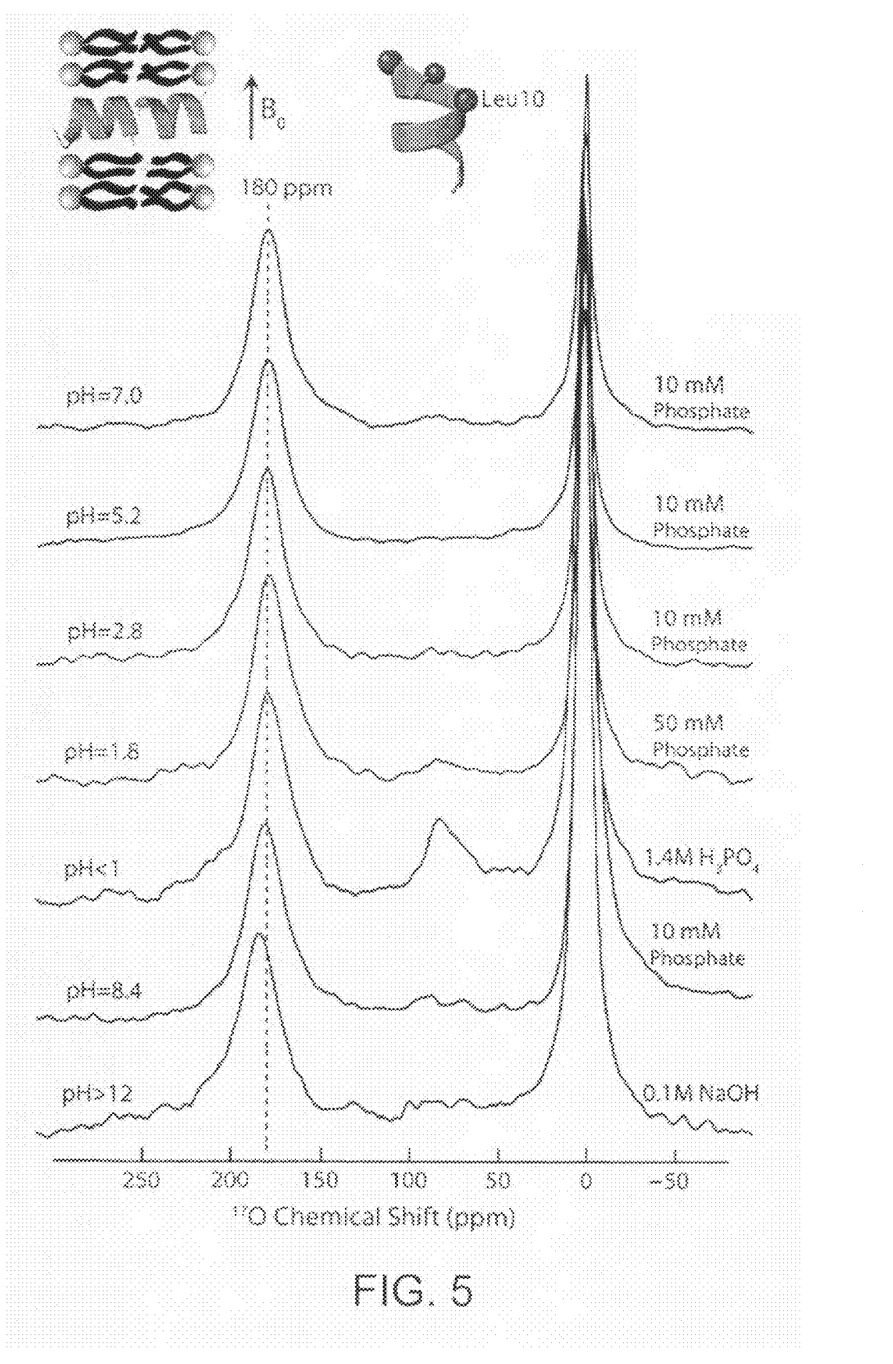
FIG. 5 depicts $^{17}$O NMR spectra of $^{17}$O-[D-Leu$^{10}$]-gA in DMPC bilayers uniformly aligned by AAO at various pH values and excess $H_2O$ with a peptide:lipid molar ratio of 1:16; other experimental conditions were as in FIG. 4; the resonance at 80 ppm at pH (1 is likely to be attributed to a natural abundance signal from a group that is protonated at very low pH. It should be noted here that the latter peak essentially disappeared on raising the pH; thus, it cannot be related to an irreversible process, such as lipid hydrolysis, that could occur at pH (1.
Figure 6:
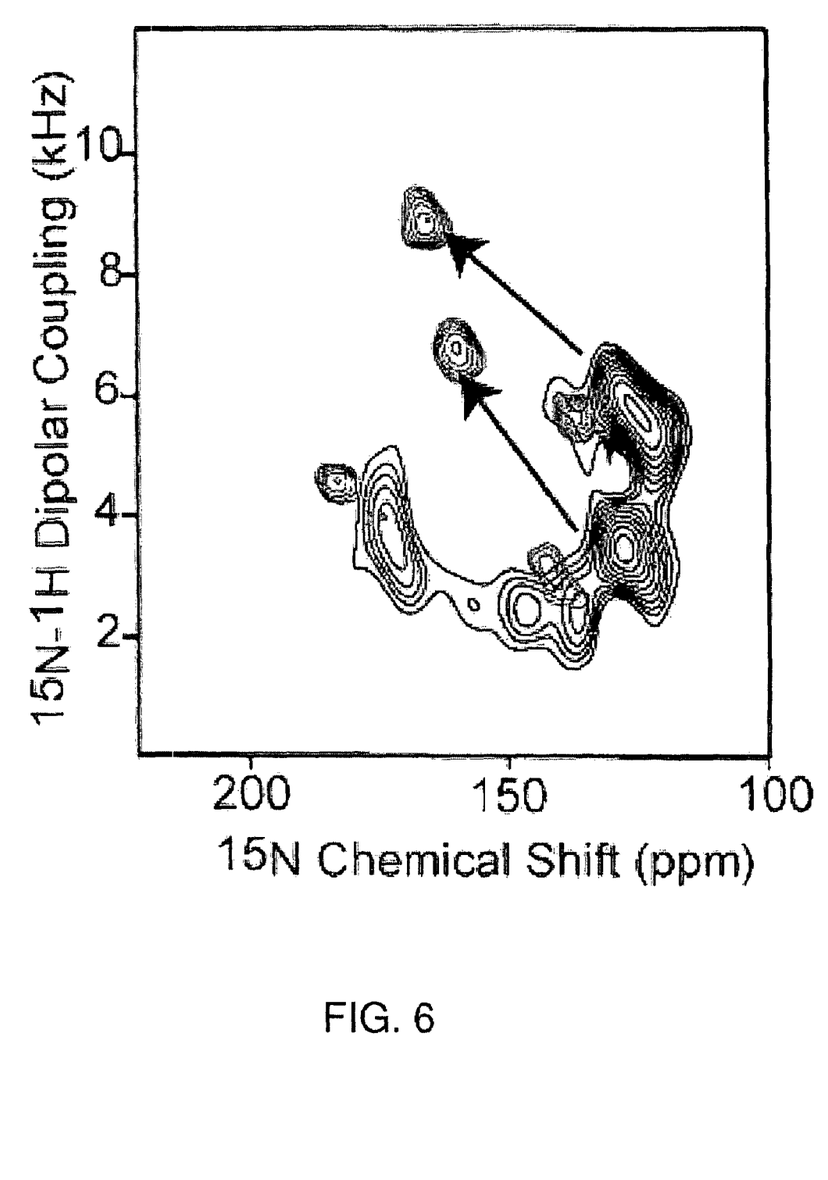
FIG. 6 demonstrates NMR signal changes upon binding drug, for example, solid-state NMR spectra of the drug target will be observed to shift, in this case spectra of the M2 Protein from Influenza A virus (a membrane protein drug target for Rimantadine and Amantadine (AMT) that are on the market today) shows dramatic changes upon Amantadine binding (red is w/AMT; blue is w/o AMT); these spectra were obtained using glass slide preparations.
Figure 7:
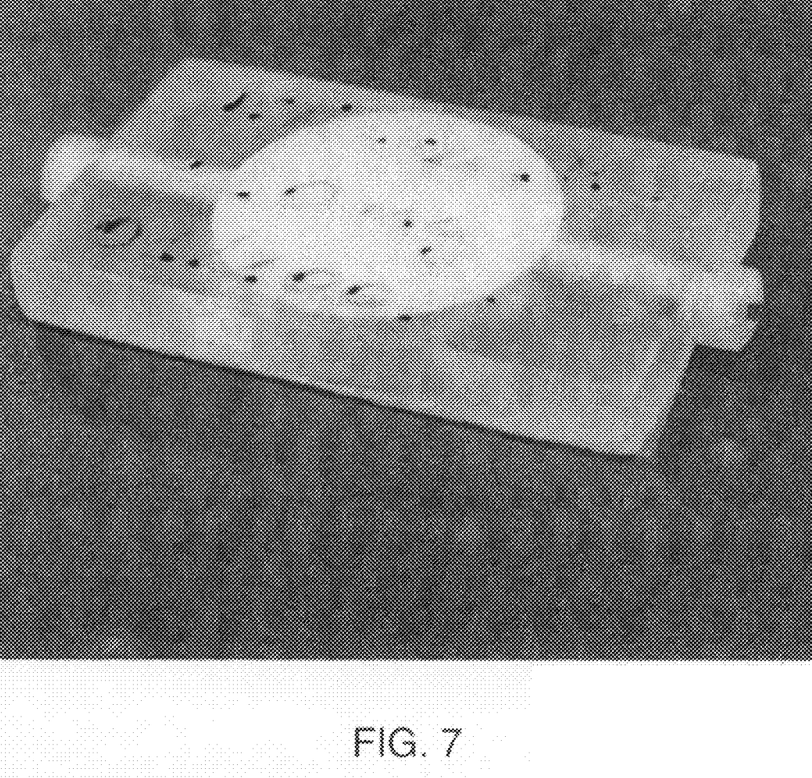
FIG. 7 is a photo of a prototype NMR sample flow cell according to the present invention.
Figure 8:
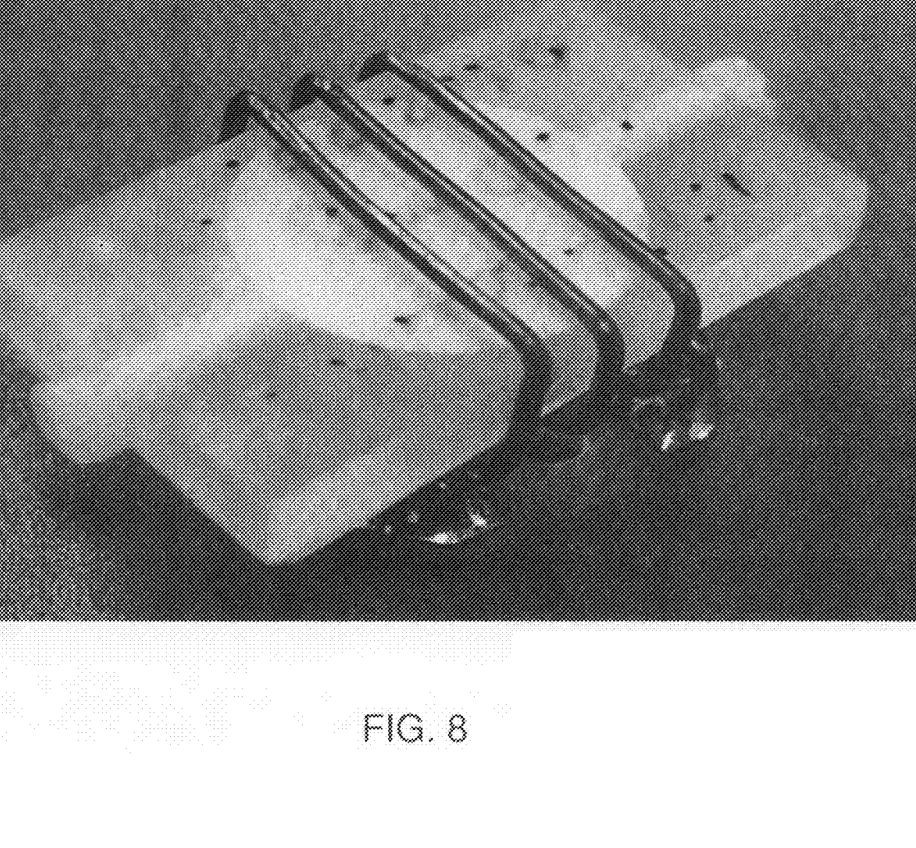
FIG. 8 shows the flow cell of FIG. 7 inserted into rectangular radio-frequency solenoid of the NMR instrument.
Figure 9:
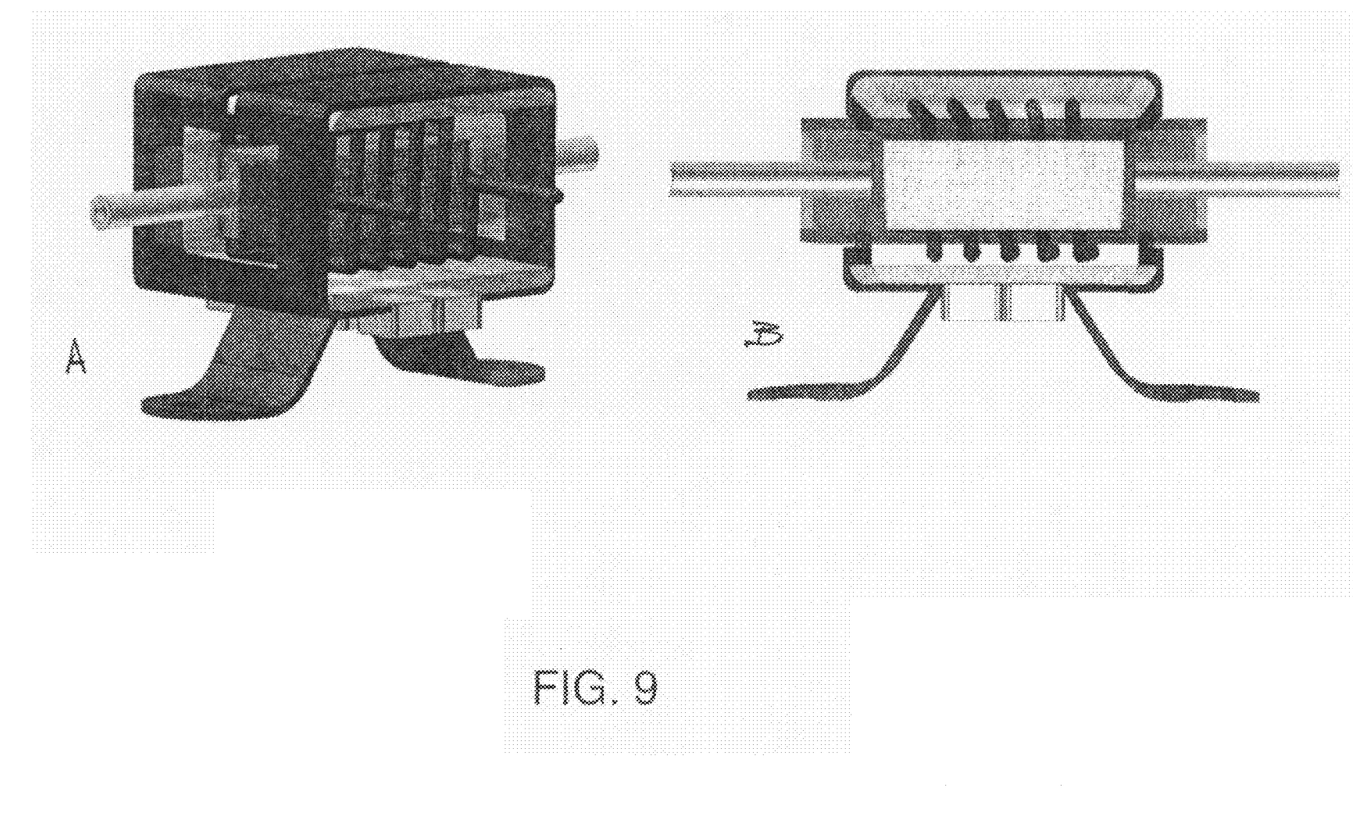
FIG. 9 provides a perspective view (A) and a cross-sectional elevation view (B) of the AAO sample-flow cell of FIGS. 7 and 8 in a low-E coil assembly; the rectangular sample cell is shown in the center in B and the end plugs are adjacent the sample cell ends.

Gramicidin A conducts a wide variety of monovalent cations including protons. Here, we provide an example of an NMR titration experiment in which we monitored the $^{17}$O resonance of D-Leu$^{10}$ carbonyl in AAO-aligned gA. The titration was started at pH=7.0 by exposing the sample to an excess (about 20 mL) of 10 mM phosphate buffer with successive pH changes to 5.2, 2.8, <1 (1.4 M H$_3$PO$_4$), 8.4, and 0.12 (0.1 M NaOH), all at T about 43° C. The entire titration experiment was carried out with the same DMPC-gA sample by immersing the stack of AAO substrate chips into a desired buffer for 20 min. Remarkably, from pH (1.0 to pH=8.4, i.e., over 7 orders of magnitude in proton concentration, no changes in the $^{17}$O peak position were observed (FIG. 5). At pH <1.0 (1.4 M H$_3$PO$_4$), the proton concentration was comparable to that of K$^+$ in FIG. 3, in which the downfield shift of 18 ppm was observed. Thus, we must conclude that proton conductance by the gA channel is not accompanied by structural changes or significant changes in the electrostatic environment measurable by $^{17}$O NMR, although the conductance of small monovalent ions such as K$^+$ does affect these parameters. A small downfield shift of the $^{17}$O line was observed at pH 12 (FIG. 5, bottom). At such an alkaline pH, one could expect initial formation of aluminum hydroxide in the pores. Overall, FIG. 5 demonstrates excellent stability of AAO-aligned lipid bilayers incorporating gramicidin A channels over a wide range of pH.

Discussion $^{31}$P NMR data presented here demonstrate full accessibility of both leaflets of nanopore-confined lipid bilayers to paramagnetic Me ions. Moreover, we have shown that the broadening of the $^{31}$P resonances is reversible by a gentle treatment of the AAO stack with the chelating agent EDTA (ethylenediaminetetraacetic acid) followed by a straightforward buffer exchange at temperatures above the main phase transition. These conditions were chosen to facilitate ion exchange because of a well-documented decrease in both lipid packing and local order parameter for lipids in the fluid phase.

Earlier $^{31}$P NMR data on accessibility of polar headgroups of POPC (1-palmitoyl-2-oleoyl-sn-glycero-3 phosphocholine) bilayers absorbed into AAO nanopores to Pr$^{3+}$ shift reagent have shown that when the bilayer is maintained in the fluid bilayer phase, the ends of some of the lipid tubules appeared to be sealed against the pore such that the ions could not access all of the phosphate groups (21). However, when the sample was lowered below the main phase transition temperature, this seal was broken, as indicated by a shift in the $^{31}$P resonances for all phosphates. In our buffer exchange NMR experiments the sample was always maintained at T=40-43° C., although we cannot exclude that the sample temperature was lowered below that of the DMPC main phase transition (T$_m$ about 24° C.) for a short time when the sample was transferred from the NMR spectrometer to a new buffer. We are investigating this issue further.

Regardless of the actual AAO-supported DMPC bilayer macrostructure and mechanism of solvent accessibility, we conclude that our experimental conditions result in fully accessible nanopore-confined lipid bilayers to water-soluble ions and/or chelating complexes such as EDTA. Importantly, we also observed that during these multiple solvent manipulations the macroscopic lipid alignment was maintained as assessed by $^{31}$P NMR. Additional $^{31}$P NMR experiments indicated that the alignment was maintained after the sample was exposed to −80° C. for a few hours and then brought back to 40° C. (not shown). This is in support of the initial work on AAO-supported lipid bilayers that showed macroscopic lipid alignment in these nanotubular structures at temperatures as low as −123° C. (16). Such exceptional stability of AAO-supported lipid bilayers to temperature variation and low-temperature storage conditions might be very advantageous over the conventional glass-plate method. Typically, the latter samples cannot be frozen or put through a freeze-thaw cycle without losing lipid alignment.

High-field $^{17}$O NMR spectroscopy of gA in hydrated DMPC bilayers that were uniformly aligned by the AAO-nanopore method yielded a single d p 178 ppm resonance for the $^{17}$O-DLeu$^{10}$ carbonyl site when the sample was maintained above T P 24° C. The observation demonstrates that when the DMPC nanotubular bilayer is in a fluid phase, the tumbling of the gA helix around the pore axis is fast enough to effectively average the $\delta 22$ and $\delta 33$ chemical shift tensor components. With further increase in temperature, the width of the carbonyl $\delta \approx 178$ ppm resonance increases slightly (most noticeable from 67° C. to 77° C.). We attribute this broadening to a contribution of nonaxial tumbling modes rather than to a decrease in the axial peptide tumbling. An increase in nonaxial tumbling is also consistent with the downfield resonance shift of up to 8 ppm at 77° C. Overall, confinement of lipid bilayers to the nanopores does not appear to have effects on the peptide tumbling, at least to an extent that would be noticeable from $^{17}$O NMR line shapes.

In our experiments this dimeric ion channel was fully accessible to the aqueous solvent, allowing a series of cation exchange and titration experiments to be carried out with physically the same sample. Specifically, we observed that reversible binding of $K^+$ resulted in a $\Delta\delta \approx 18$ ppm down-field shift of the $^{17}O$ resonance at $\delta_\perp$ that is about half of the 40 ppm shift at $\delta\|$ reported for DMPC-gA samples aligned by glass slides (29). This difference in Dd arises from the orientation of the gA channel with respect to the magnetic field, $B_0$: for glass-aligned samples the ion channel was parallel to $B_0$, and the $^{17}O$ resonance was dictated by $\delta\|=\delta_{11}$, whereas for the AAO-aligned sample, the channel was perpendicular to $B_0$, so the resonance was centered at $\delta_\perp \approx \delta_{22}+\delta_{33}$). The later two tensorial components are less sensitive to ion binding than $\delta_{11}$ (33). The changes in $\delta\|$ and $\delta_\perp$ could be induced by polarizabilty effects when $K^+$ is solvated by the $Leu^{10}$ carbonyl. Solvation of $K^+$ by the channel is known to affect the individual principal components of the $^{15}N$ chemical shift tensor of $Trp^{11}$ in the same peptide plane with the $Leu^{10}$ carbonyl oxygen (28). Additionally, a structural change by just a few degrees of tilt of the peptide plane toward the ion can cause a decrease of $\delta\|$ and an increase in $\delta_\perp$ (34). It is also possible that the $^{17}O$ resonance we observed at 2.4 M KCl contains a fraction of the residual unshifted resonance corresponding to unbound $K^+$. More studies are needed to evaluate these effects.

Exposing the gA channel to a high proton concentration did not result in any measurable shift of the $^{17}O$-D-$Leu^{10}$ carbonyl resonance. This unexpected result points to a difference in mechanisms for monovalent metal ion and proton conduction by the gA pore.

The experiments described here are made possible by the use of nanoporous AAO-supported bilayers. Typically, macroscopically aligned glass-supported lipid bilayers cannot be immersed in a buffer without losing much of the lipid in the form of vesicles. Whereas AAO nanopores host only a few individual lipid bilayers, the glass plates sandwich a few thousand bilayers, a three order of magnitude difference. As a result, the AAO-supported bilayer sample is more stable, as demonstrated by the variable temperature experiments up to 77° C. To maintain stability, the hydration level of the glass-supported samples is lower than that of the MO-alignment method where maximal hydration is coupled with good macroscopic alignment and insignificant lipid loss on changing the solvent environment. The aligned nanoporous AAO substrate provides the advantages of fast accessibility by solute molecules, reversible ion exchange, and titration experiments with physically the same sample of membrane protein. Thus, one can achieve significantly better control of the bilayers by exposing the lipid nanotubes to various solutions and fine-tuning the bilayer properties by exchanging solvents with the bulk solution. In contrast, the aqueous phase of the lipid bilayers that are sandwiched between glass plates cannot be manipulated with the same ease. Typically, only gaseous exchange experiments can be carried out (35), and those are typically slower and significantly more difficult to control, especially for hygroscopic lipids.

The use of AAO-supported bilayers offers distinct advantages over both glass-slide-supported bilayers and magnetically aligned bicelle samples. The fraction of the sample volume occupied by the hydrated lipid-protein sample is approximately the same in all three classes of aligned samples. The significant fraction of MO or glass is offset by the high aqueous fraction in the bicelle samples. The AAO- and glass-supported samples have the advantage over bicelles where there is considerable isotropic averaging leading to an order parameter of approximately 0.8. The AAO and bicelle samples have the advantage that sample conditions can be easily changed without remaking the entire sample. AAO substrate-aligned samples are also advantageous in experiments with hydrated bilayer samples because of their intrinsic ability to suppress thermal gradients arising in NMR experiments at high RF power and frequencies (36). Indeed, the thermal conductivity of alumina is about 25-35 W $m^{-1}$ $K^{-1}$ (37) versus only about 0.6 W $m^{-1}K^{-1}$ for water (38). It also compares very favorably with thermal conductivity of glass of about 1.1 W $m^{-1}K^{-1}$ (37).

Although lipid formulations for bicelles that align in external magnetic field under acidic and basic pH values and extended temperature ranges have been reported in the literature (9, 10), the choices of lipid composition for such systems remain limited. Experiments carried out at the authors' NCSU laboratory indicate that macroscopically aligned lipid nanotubular bilayers can be assembled from various lipids including anionic and also lipid-cholesterol mixtures (Alaouie, A. M. and A. I. Smirnov, unpublished data). Moreover, differential scanning calorimetry data have shown that the bilayer thermodynamics is perturbed to a much smaller degree than for lipid bilayers formed on planar substrates (19, 20). Specifically, the main phase transition temperature for AAO-supported DMPC was found to be the same as for unsupported multilamellar bilayers (20). Thus, it appears that the lipid bilayers in nanoporous AAO can be maintained in the same thermodynamic phase at the same temperature as the unsupported bilayers. From this perspective, AAO-supported bilayers should provide a better mimic for native bilayers in terms of thermodynamic properties and hydrophobic matching as compared with bicelles that have altered phase behavior.

One limitation of the AAO nanopore method is that only a single unique orientation of the bilayer normal with respect to $B_0$ can be achieved by aligning the nanopores along $B_0$. The perpendicular orientation would result in broad NMR line shapes determined by a cylindrical powder pattern. "Unflipped" bicelles also align with the bilayer normal perpendicular to the external magnetic field, the same bilayer orientation we employed for AAO-supported samples. Although bicelles can be flipped by adding lanthanides directly to lipid-protein systems (7) or to a chelating phospholipid (39), further studies are needed to find whether such manipulation of the bilayer-water interface would affect bilayer properties and/or protein rotational diffusion.

Summary

We conclude by remarking on the convenience of utilizing nanoporous AAO substrates for aligning lipid bilayers containing membrane proteins for solid-state NMR studies. In our experience, the AAO strips can be handled easily because the bilayer surfaces are well protected by the rigid structure of the substrate. The stack can be disassembled and reassembled as needed and stored in a −80° C. freezer for a long time without losing lipid and membrane peptide alignment. These properties are maintained in a very broad pH range (1-12) and temperatures as high as 70° C. We also demonstrate that the surfaces of both leaflets of such bilayers are fully accessible to aqueous solutes. Thus, high hydration levels as well as pH and desirable ion and/or drug concentrations could be easily maintained and modified as desired in a series of experiments with the same preparation of membrane protein sample. We are proposing that a large number of solid-state NMR-based studies will benefit significantly from the method described here. It will be possible to carry out a wide range of titration experiments with higher precision, shorter time, and less protein because the sample can be reused effectively without redepositing it onto the substrate. The latter feature is especially important for isotopically labeled membrane proteins that are difficult and/or expensive to express in large quantities. Another type of NMR experiment that will benefit significantly from faster solution delivery is $^2$H exchange: fully accessible AAO nanochannels will provide better temporal resolution than samples aligned on glass plates (40, 41). Designing flow-through systems and integrating those with existing NMR probes would automate solvent-exchange experiments and further improve temporal resolution. Structure-function and drug-screening solid-state NMR studies could then be carried out by incorporating the protein of interest into AAO-supported lipid nanotubes and exposing the sample to various drugs and other solute molecules. In such studies a sequence of solutions could be utilized to study competitive binding or sequential conformations of membrane proteins.

In the drawings and specification, there have been disclosed typical preferred embodiments of the invention, and although specific terms may have been used, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES CITED

1. Vinogradova, O., P. Badola, L. Czerski, F. D. Sonnichsen, and C. R. Sanders. 1997. *Escherichia coli* diacylglycerol kinase: A case study in the application of solution NMR methods to an integral membrane protein. Biophys. J. 72:2688-2701.
2. Bogdanov, M., P. N. Heacock, and W. Dowhan. 2002. A polytopic membrane protein displays a reversible topology dependent on membrane lipid composition. EMBO J. 21:2107-2116.
3. Park, S. H., A. A. Mrse, A. A. Nevzorov, A. A. DeAngelis, and S. J. Opella. 2006. Rotational diffusion of membrane proteins in aligned phospholipid bilayers by solid-state NMR spectroscopy. J. Magn. Reson. 178:162-165.
4. Moll, F. II, and T. Cross. 1990. Optimizing and characterizing alignment of oriented lipid bilayers containing gramicidin D. Biophys. J. 57:351-362.
5. Sanders, C. R., B. J. Hare, K. P. Howard, and J. H. Prestegard. 1994. Magnetically-oriented phospholipid micelles as a tool for the study of membrane-associated molecules. Prog. Nucl. Magn. Reson. Spectrosc. 26:421-444.
6. Sanders, C. R., and G. C. Landis. 1995. Reconstitution of membrane-proteins into lipid-rich bilayered mixed micelles for NMR-studies. Biochemistry. 34:4030-4040.
7. Prosser, R. S., S. A. Hunt, J. A. DiNatale, and R. R. Vold. 1996. Magnetically aligned membrane model systems with positive order parameter: Switching the sign of S-zz with paramagnetic ions. J. Am. Chem. Soc. 118:269-270.
8. DeAngelis, A. A., A. A. Nevzorov, S. H. Park, S. C. Howell, A. A. Mrse, and S. J. Opella. 2004. High-resolution NMR spectroscopy of membrane proteins in aligned bicelles. J. Am. Chem. Soc. 126:15340-15341.
9. Ottiger, M., and A. Bax. 1999. Bicelle-based liquid crystals for NMR measurement of dipolar couplings at acidic and basic pH values. J. Biomol. NMR. 13:187-191.
10. Cavagnero, S., H. J. Dyson, and P. E. Wright. 1999. Improved low pH bicelle system for orienting macromolecules over a wide temperature range. J. Biomol. NMR. 13:387-391.
11. Hallock, K. J., K. H. Wildman, D. K. Lee, and A. Ramamoorthy. 2002. An innovative procedure using a sublimable solid to align lipid bilayers for solid-state NMR studies. Biophys. J. 82:2499-2503.
12. Marassi, F. M., and K. J. Crowell. 2003. Hydration-optimized oriented phospholipid bilayer samples for solid-state NMR structural studies of membrane proteins. J. Magn. Reson. 161:64-69.
13. Sizun, C., and B. Bechinger. 2002. Bilayer sample for fast or slow magic angle oriented sample spinning solid-state NMR spectroscopy. J. Am. Chem. Soc. 124:1146-1147.
14. Opella, S. J., and F. M. Marassi. 2004. Structure determination of membrane proteins by NMR spectroscopy. Chem. Rev. 104:3587-3606.
15. Walian, P., T. A. Cross, and B. K. Jap. 2004. Structural genomics of membrane proteins. Genome Biol. 5:215.
16. Smirnov, A. I., and O. G. Poluektov. 2003. Substrate-supported lipid nanotube arrays. J. Am. Chem. Soc. 125:8434-8435.
17. Chekmenev, E. Y., J. Hu, P. L. Gor'kov, W. W. Brey, T. A. Cross, A. Ruuge, and A. I. Smirnov. 2005. N-15 and P-31 solid-state NMR study of transmembrane domain alignment of M2 protein of influenza A virus in hydrated cylindrical lipid bilayers confined to anodic aluminum oxide nanopores. J. Magn. Reson. 173:322-327.
18. Lorigan, G. A., P. C. Dave, E. K. Tiburu, K. Damodaran, S. Abu-Baker, E. S. Karp, W. J. Gibbons, and R. E. Minto. 2004. Solid-state NMR spectroscopic studies of an integral membrane protein inserted into aligned phospholipid bilayer nanotube arrays. J. Am. Chem. Soc. 126:9504-9505.
19. Alaouie, A. M., and A. I. Smirnov. 2006. Formation of a ripple phase in nanotubular dimyristoylphosphatidylcholine bilayers confined inside nanoporous aluminum oxide substrates observed by DSC. Langmuir. 22:5563-5565.
20. Alaouie, A. M. and A. I. Smirnov. 2005. Cooperativity and kinetics of phase transitions in nanopore-confined bilayers studied by differential scanning calorimetry. Biophys. J. 88:L11-L13.
21. Gaede, H. C., K. M. Luckett, I. V. Polozov, and K. Gawrisch. 2004. Multinuclear NMR studies of single lipid bilayers supported in cylindrical aluminum oxide nanopores. Langmuir. 20:7711-7719.
22. Wattraint, O., D. E. Warschawski, and C. Sarazin. 2005. Tethered or adsorbed supported lipid bilayers in nanotubes characterized by deuterium magic angle spinning NMR spectroscopy. Langmuir. 21:3226-3228.
23. Doyle, D. A., J. M. Cabral, R. A. Pfuetzner, A. L. Kuo, J. M. Gulbis, S. L. Cohen, B. T. Chait, and R. MacKinnon. 1998. The structure of the potassium channel: Molecular basis of K1 conduction and selectivity. Science. 280:69-77.
24. MacKinnon, R. 2003. Potassium channels. FEBS Lett. 555:62-65.
25. Busath, D. D. 1993. The use of physical methods in determining gramicidin channel structure and function. Annu. Rev. Physiol. 55:473-501.
26. Ketchem, R. R., W. Hu, and T. A. Cross. 1993. High-resolution conformation of gramicidin-a in a lipid bilayer by solid-state NMR. Science. 261:1457-1460.
27. Ketchem, R. R., B. Roux, and T. A. Cross. 1997. High-resolution polypeptide structure in a lamellar phase lipid environment from solid state NMR derived orientational constraints. Structure. 5:1655-1669.

28. Tian, F., and T. A. Cross. 1999. Cation transport: An example of structural based selectivity. J. Mol. Biol. 285: 1993-2003.
29. Hu, J., E. Y. Chekmenev, Z. H. Gan, P. L. Gor'kov. S. Saha. W. W. Brey, and T. A. Cross. 2005. Ion solvation by channel carbonyls characterized by 0-17 solid-state NMR at 21 T. J. Am. Chem. Soc. 127:11922-11923.
30. Fu, R., W. W. Brey, K. Shetty, P. Gor'kov, S. Saha, J. R. Long, S. C. Grant, E. Y. Chekmenev, J. Hu, Z. Gan, M. Sharma, F. Zhang, et al. 2005. Ultra-wide bore 900 MHz high-resolution NMR at the National High Magnetic Field Laboratory. J. Magn. Reson. 177:1-8.
31. Gowen, J. A., J. C. Markham, S. E. Morrison, T. A. Cross, D. D. Busath, E. J. Mapes, and M. F. Schumaker. 2002. The role of Trp side chains in tuning single proton conduction through gramicidin channels. Biophys. J. 83:880-898.
32. Bystrov, V. F., N. I. Dubrovin, L. I. Barsukov, and L. D. Bergelson. 1971. NMR differentiation of internal and external phospholipid membrane surfaces using paramagnetic Mn21 and Eu31 Ions. Chem. Phys. Lipids. 6:343-350.
33. Chekmenev, E. Y., K. W. Waddell, J. Hu, Z. Gan, R. J. Wittebort, and T. A. Cross. 2006. Ion binding study by 170 solid-state NMR spectroscopy in the model peptide Gly-Gly-Gly at 19.6T. J. Am. Chem. Soc. 128:9849-9855.
34. Tian, F., and T. A. Cross. 1998. Cation binding induced changes in N-15 CSA in a membrane-bound polypeptide. J. Magn. Reson. 135: 535-540.
35. Cotten, M., R. Fu, and T. A. Cross. 1999. Solid-state NMR and hydrogen-deuterium exchange in a bilayer-solubilized peptide: Structural and mechanistic implications. Biophys. J. 76:1179-1189.
36. Li, C. G., Y. M. Mo, J. Hu, E. Chekmenev, C. L. Tian, F. P. Gao, R. Q. Fu, P. Gor'kov, W. Brey, and T. A. Cross. 2006. Analysis of RF heating and sample stability in aligned static solid-state NMR spectroscopy. J. Magn. Reson. 180:51-57.
37. Material property data. http://www.matweb.com/. [Online].
38. Thermal conductivity data. http://www.EngineeringToolBox.com/. [Online].
39. Prosser, R. S., V. B. Volkov, and I. V. Shiyanovskaya. 1998. Novel chelate-induced magnetic alignment of biological membranes. Biophys. J. 75:2163-2169.
40. Huo, S., S. Arumugam, and T. A. Cross. 1996. Hydrogen exchange in the lipid bilayer-bound gramicidin channel. Solid State Nucl. Magn. Reson. 7:177-183.
41. Tian, C. L., P. F. Gao, L. H. Pinto, R. A. Lamb, and T. A. Cross. 2003. Initial structural and dynamic characterization of the M2 protein transmembrane and amphipathic helices in lipid bilayers. Protein Sci. 12:2597-2605.

That which is claimed:

1. A method for detecting a candidate drug binding to a cell membrane protein by solid-state NMR, the method comprising:
   self-assembling a composition containing lipids and a cell membrane protein into a lipid bilayer in nanopores of a plurality of anodic aluminum oxide (AAO) support substrates;
   positioning said AAO support substrates in a solid-state NMR flow cell;
   associating said solid-state NMR flow cell with a radio-frequency solenoid in an NMR instrument so as to orient the composition such that a surface of the lipid bilayer is substantially parallel to the NMR instrument's magnetic field;
   passing a first solution containing one or more candidate drugs through the flow cell so as to contact the cell membrane protein;
   generating a first solid-state NMR spectrum for said cell membrane protein;
   passing a second solution free of candidate drugs through the flow cell so as to wash the cell membrane protein of bound and unbound candidate drugs;
   generating a second solid-state NMR spectrum for said washed cell membrane protein; and
   detecting a shift in resonance frequencies of the solid-state NMR spectrum of said cell membrane protein from the first spectrum to the second spectrum as an indicator of protein binding by at least one candidate drug.

2. A method for detecting a candidate drug binding to a cell membrane protein by shifting solid-state NMR spectra of the protein, the method comprising:
   self-assembling a composition containing lipids and a cell membrane protein into a lipid bilayer in nanopores of an anodic aluminum oxide (AAO) support substrate;
   positioning said AAO support substrates substrate in a solid-state NMR flow cell;
   associating said flow cell with a radio-frequency solenoid in an NMR instrument so as to align the lipid bilayer with the NMR instrument's magnetic field;
   generating a first solid-state NMR spectrum for said cell membrane protein;
   passing a solution containing one or more candidate drugs through said flow cell so as to contact the cell membrane protein;
   generating a second solid-state NMR spectrum for said cell membrane protein; and
   detecting a shift in the solid-state NMR spectrum of said cell membrane protein from the first spectrum to the second spectrum as an indicator of protein binding by at least one candidate drug.

* * * * *

UNITED STATES PATENT AND TRADEMARK OFFICE
CERTIFICATE OF CORRECTION

| | | |
|---|---|---|
| PATENT NO. | : 7,678,546 B1 | Page 1 of 1 |
| APPLICATION NO. | : 11/865302 | |
| DATED | : March 16, 2010 | |
| INVENTOR(S) | : Cross et al. | |

It is certified that error appears in the above-identified patent and that said Letters Patent is hereby corrected as shown below:

In the Specification

Column 1, Line 10

Insert: -- STATEMENT OF GOVERNMENT INTEREST

This invention was made with government support under DMR9016241 and MCB0235774 awarded by the National Science Foundation, under DE-FG02-02ER15354 awarded by Department of Energy, and under GM072897 awarded by National Institutes of Health. The government has certain rights in the invention. --

Signed and Sealed this
Eighth Day of July, 2014

Michelle K. Lee
*Deputy Director of the United States Patent and Trademark Office*